United States Patent [19]

Walda

[11] 4,249,923
[45] Feb. 10, 1981

[54] CARDIOPLEGIC FLUID REFRIGERATION AND DELIVERY SYSTEM

[76] Inventor: Kim L. Walda, 1468 Rosewood, Ann Arbor, Mich. 48104

[21] Appl. No.: 56,408

[22] Filed: Jul. 10, 1979

[51] Int. Cl.³ .............................................. F67D 5/62
[52] U.S. Cl. .......................................... 62/394; 62/78; 62/518; 128/214 A; 128/399; 165/169
[58] Field of Search ..................... 62/394, 514 R, 518, 62/78; 165/46, 169; 128/214 A, 399

[56] References Cited

U.S. PATENT DOCUMENTS

| | | | |
|---|---|---|---|
| 1,960,417 | 5/1934 | Pain, Jr. | 128/214 A |
| 1,990,325 | 2/1935 | Hopkes | 62/394 |
| 2,110,022 | 3/1938 | Kliesrath | 165/46 |
| 2,180,237 | 11/1939 | Henderson | 62/518 |
| 2,623,367 | 12/1952 | Morrison | 62/78 |
| 2,627,728 | 2/1953 | Levin | 62/78 |
| 2,825,338 | 3/1958 | Schnepf et al. | 165/46 |
| 2,958,212 | 11/1960 | Cohrt | 62/518 |
| 3,247,851 | 4/1966 | Seibert | 128/214 A |

Primary Examiner—Ronald C. Capossela
Attorney, Agent, or Firm—Olsen and Stephenson

[57] ABSTRACT

A refrigeration and delivery system for chilling a cardioplegic fluid contained in a receptacle, for maintaining the fluid at a predetermined temperature and for delivering the fluid to a patient as needed. The refrigeration and delivery system consists of a refrigerator cabinet having an evaporator disposed in an internal chilling compartment for supporting the fluid receptacle. The evaporator has a heat transfer surface in direct engagement with the receptacle to facilitate the conduction of heat from the fluid to the evaporator. The receptacle has inlet and outlet ports connected by recirculation tubing which provides a flow path to recirculate the fluid insuring that chilled fluid is contained in the recirculation tubing. A discharge tube is connected to the recirculation tubing and when opened allows the chilled cardioplegic fluid to be administered to the patient.

18 Claims, 6 Drawing Figures

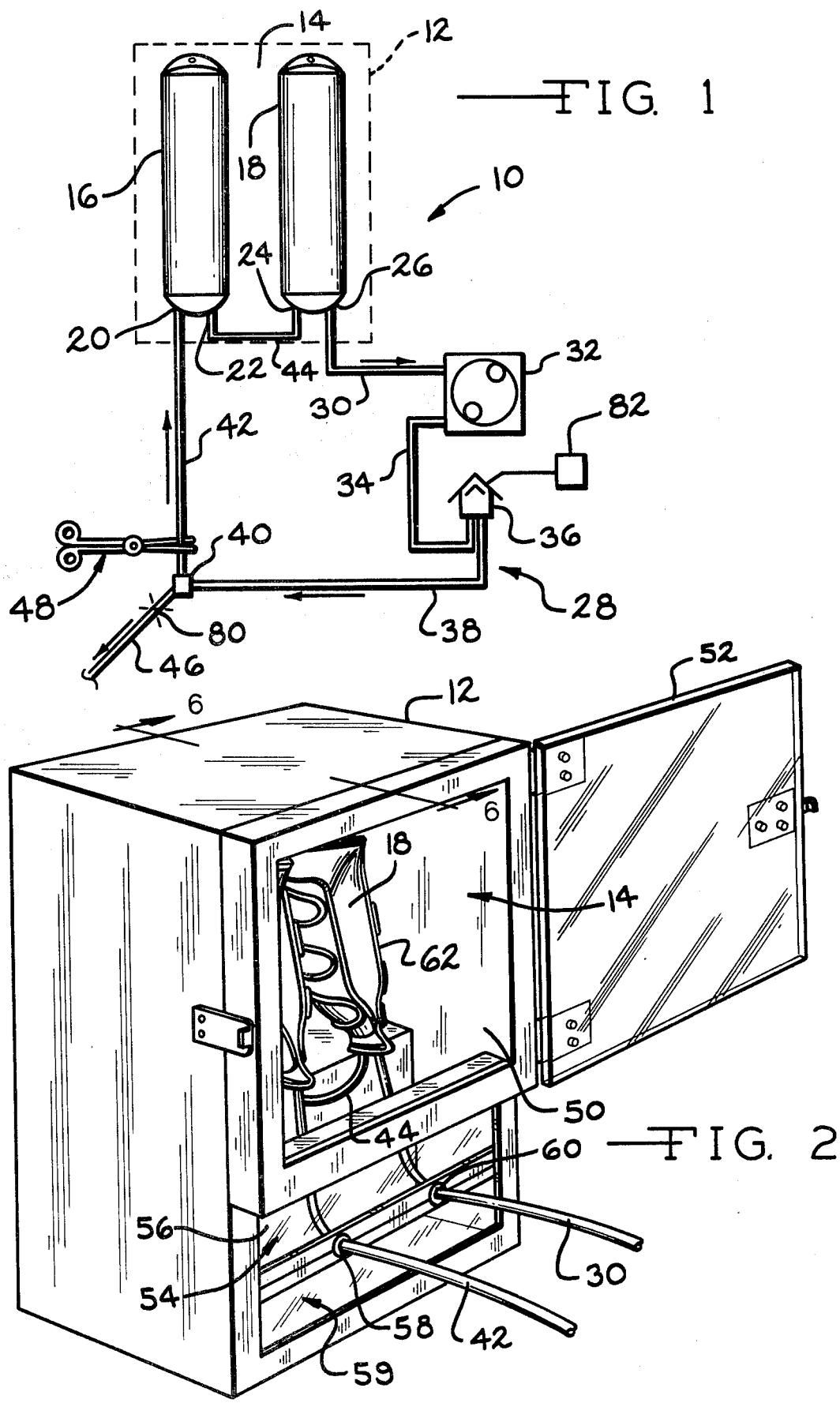

CARDIOPLEGIC FLUID REFRIGERATION AND DELIVERY SYSTEM

BACKGROUND OF THE INVENTION

The present invention relates generally to a fluid refrigeration and delivery system, and more particularly, to a fluid refrigeration and delivery system used in connection with surgical or other medical procedures in which chilled fluid is periodically administered to a patient.

Heart surgery often requires that the surgeon terminate the functioning of the heart without damaging the heart muscle. This is accomplished by injecting a chilled cardioplegic fluid through a catheter into the aortic root of the heart. The chilled cardioplegic fluid lowers the temperature of the heart thereby causing it to cease pumping.

The conventional mode of chilling and administering the cardioplegic fluid is manifestly inadequate. The cardioplegic fluid, contained in the conventional IV plastic bag, is chilled in a refrigerator prior to the operation. Shortly prior to the operation the IV bag containing the chilled cardioplegic fluid is removed from the refrigerator, placed in a bucket of ice, and brought to the operating room. When it is time to administer the cardioplegic fluid, the IV bag is hung on an IV pole. A plastic tube is connected to the discharge outlet of the IV bag and to a catheter. The tubing is clamped to restrain the flow of cardioplegic fluid until the surgeon is ready to administer it.

The surgeon, prior to administering the cardioplegic fluid to the heart, must initially purge the tubing of the fluid because its temperature will rise quickly to an unacceptable level due to the warm tubing. After purging a sufficient quantity of cardioplegic fluid through the tubing, chilled fluid is available for administration to the patient. The surgical procedure begins as soon as a sufficient quantity of chilled cardioplegic fluid has been injected into the heart to cause it to cease pumping. The temperature of the heart gradually rises and prior to attaining a temperature level that would cause it to start functioning, the surgeon must reinsert the catheter and supply another quantity of chilled cardioplegic fluid to the heart. However, during the time span after the initial administration of the cardioplegic fluid, the fluid in the tubing begins to warm up as does the fluid in the IV bag which is subjected to room temperature, although its temperature increases at a slower rate. The surgeon must therefore again purge the warmed fluid from the tubing so that the cooler fluid in the bag is available for administration to the patient.

There are numerous problems associated with such a crude refrigeration and delivery system. First, there is no temperature control for the cardioplegic fluid. Since the IV bag on an IV pole at room temperature, the fluid's temperature gradually rises, and since the IV bag is stored in a bucket of ice, its initial temperature can be no lower than about 0° C. Consequently, the effectiveness of the cardioplegic fluid decreases rapidly as the surgery progresses. Often even though the fluid is only partially used, a fresh IV bag from the ice bucket must be used because the fluid in the first bag becomes too warm. The employment of ice for cooling is unsanitary and inconvenient. There is also a problem of maintaining ideal sterile conditions in the vicinity of the operating table. Also, moisture condenses on the IV bag causing difficulty in visually monitoring the amount of fluid used. Finally, the purging procedure to rid the tubing of warmed cardioplegic fluid wastes time. The heart may enter a hypoxic condition creating a situation in which damage to the heart muscle may result.

It is the object of the present invention, therefore, to provide a fluid refrigeration and delivery system particularly adapted for use in the health care field.

It is another object of the present invention to provide a refrigeration system having novel evaporator members for supporting IV bags to promote conduction of heat from a solution in the bag to the evaporator sleeve.

SUMMARY OF THE INVENTION

The present invention overcomes the deficiencies of present systems for administering cardioplegic fluid to the patient by providing a cardioplegic fluid refrigeration and delivery system in which cardioplegic fluid is chilled and can be administered expeditiously to the patient. The refrigeration system consists of a refrigerator cabinet having an internal chilling zone or compartment in which cooling coils are disposed. A tubular evaporator sleeve is disposed in the chilling compartment in direct engagement with the cooling coils so that the cooling coils substantially surround the evaporator sleeve. The tubular evaporator sleeve is located in an upright position and receives an IV bag containing cardioplegic fluid and it essentially surrounds the IV bag. The direct engagement of the IV bag with the tubular evaporator sleeve promotes the conduction of heat from the fluid to the evaporator sleeve and to the cooling medium circulating through the cooling coils.

The refrigerator cabinet has a first access opening to the chilling compartment which is closed by a transparent door enabling the contents of the fluid in the IV bag to be monitored. A second opening is positioned below the first opening and is closed by a sliding door that is movable up and down. The IV bag has inlet and outlet ports which are connected by a closed loop recirculation tube so that the cardioplegic fluid can be circulated by means of a pump from the IV bag through the tubing and back to the IV bag to supply chilled fluid in the tubing at all times. A discharge tube is connected to the recirculation tubing between the inlet and outlet ports of the IV bag. When the cardioplegic fluid is not needed, a clamp closes the discharge tube while the pump operates to recirculate the fluid through the tubing and the IV bag. When the cardioplegic fluid is to be administered to the patient, the tubing is clamped at a point upstream of the connection of the discharge tube to the recirculation tubing and the discharge tube is opened so that chilled fluid is administered to the patient. Consequently, the temperature of the cardioplegic fluid is maintained at a predetermined value and the fluid in the recirculation tubing remains chilled even though a substantial portion of the recirculation tubing is outside the chilling compartment allowing the immediate administration of the cardioplegic fluid to the patient to obviate the purging procedure.

Further objects, features and advantages of the present invention will become apparent from a consideration of the following description when taken in connection with the appended claims and the accompanying drawing in which:

FIG. 1 diagrammatically illustrates the cardioplegic fluid refrigeration and delivery system of the present invention;

FIG. 2 is a perspective view of the refrigerator cabinet of the present invention in which a pair of IV bags containing cardioplegic fluid are disposed;

Figure 3:
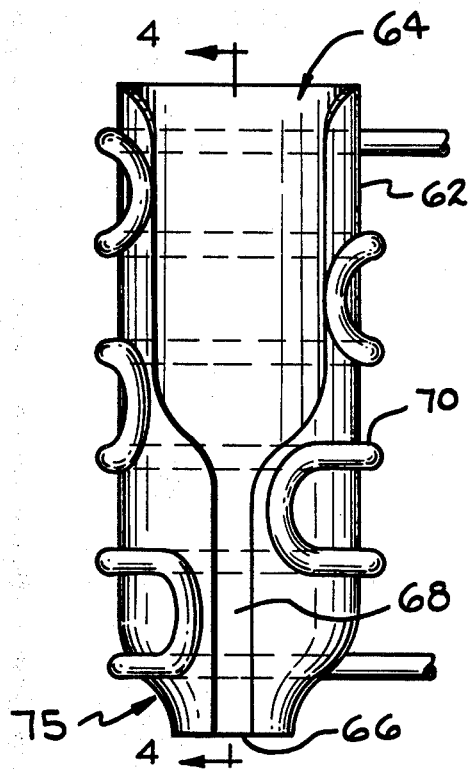
FIG. 3 is a front elevational of a sleeve evaporator used for supporting an IV bag in the refrigerator cabinet.

Referring to the drawing, the cardioplegic fluid refrigeration and delivery system, indicated generally at 10, is shown in FIG. 1 consisting of a refrigerator cabinet 12 having an internal chilling zone or compartment 14 in which a pair of serially connected IV bags 16 and 18 are disposed. The IV bags 16 and 18 contain a cardioplegic solution which when chilled and administered to the heart of the patient causes the heart to cease functioning without damaging the tissue of the heart. The IV bag 16 has an inlet port 20 and an outlet port 22 and the IV bag 18 has an inlet port 24 and an outlet port 26.

A recirculating passageway loop 28, formed of conventional plastic tubing, connects the outlet 26 of the IV bag 18 with the inlet 20 of the IV bag 16. The passageway loop 28, a substantial portion of which is outside the chilling compartment 14, includes a branch 30 which connects the outlet port 26 of the IV bag 18 with a pump 32. A branch 34 of the passageway loop 28 connects the pump 32 with an air trap 36 which insures that all air in the fluid will be extracted prior to delivery of the fluid to the patient. A branch 38 connects the outlet port of the air trap 36 with a juncture 40 in the loop 28. A branch 42 connects the juncture 40 with the inlet 20 and a branch 44 connects the outlet port 22 of the IV bag 16 with the inlet port 24 of the IV bag 18 so that the branches 30, 34, 38, 42 and 44 form the recirculation loop 28, a substantial portion of which is outside the chilling zone 14. Thus, the fluid in the loop 28 continually absorbs the heat from the warmer room temperature and must be extracted to keep the fluid chilled.

A discharge conduit 46 is connected to the recirculation loop 28 at the juncture 40 and is connected to a catheter (not shown) that is insertable into the heart of the patient. A clamp 48 which forms a flow restrictor means is employed to selectively close the passageway loop 28 at a position on the branch upstream of the juncture 40 and to close the discharge conduit 46 when it is clamped thereto. Although the refrigeration and delivery system 10 of the present invention is illustrated using two IV bags 16 and 18, it is within the scope of this invention to utilize either a single IV bag or more than two IV bags with the IV bags being serially connected. The more IV bags used, a greater fluid capacity is available which may avoid bag changes during lengthy procedures.

Figure 6:
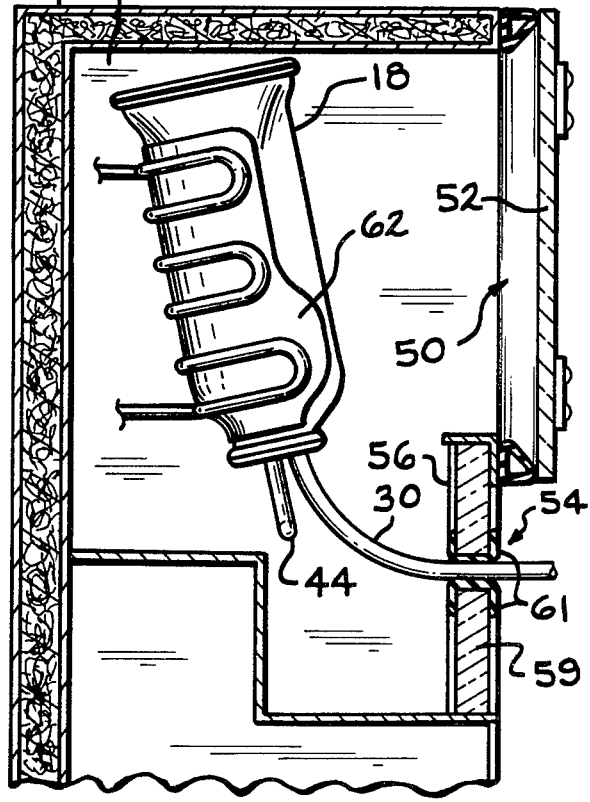
FIG. 6 is a side elevational view of the refrigerator cabinet of the invention taken substantially from line 6—6 in FIG. 2 showing the positioning of the sleeve evaporator and an IV bag in the chilling compartment of the refrigerator cabinet.

The refrigerator cabinet 12, as shown in FIGS. 2 and 6, has an access opening 50 to the chilling compartment 14. The access opening 50 is closed by a transparent door 52 which is hingedly connected on the cabinet 12 and which is preferably formed of Plexiglas enabling a person to view the interior of the compartment 14. A second access opening 54 is located below the first opening 50 and is opened and closed by a vertically slidable door 56 which is held in place by tracks (not shown) on each side of the opening 54. The tubing branches 42 and 30 extend through the second access opening 54 and are retained in circular openings 58 and 60. The openings 58 and 60 are formed by hemispherical grooves in a lower support 59 aligned with hemispherical grooves in the bottom of the door 56. Suitable gasket material 61 in the openings 58 and 60 surrounds the tubing branches 30 and 42 to prevent the escape of cold air from the compartment 14. The second access opening 54 allows the recirculation tubing 28 to be connected to the IV bags without opening the door 52.

The IV bags 16 and 18 are supported in the chilling compartment 14 by tubular sleeve members 62. Each tubular sleeve member 62 (FIGS. 2-6) is formed from material having a high heat conductivity characteristic such as copper. The tubular or cylindrical sleeve member 62 has open ends 64 and 66 with a longitudinal opening 68 extending between the ends 64 and 66. The longitudinal opening 68 forms a slot near the lower end 66 and flares outwardly near the center of the sleeve 62 to form a larger opening and enables an IV bag while connected to its tubing to be inserted and supported by the evaporator sleeve 62 by moving the IV bag and tubing laterally through the opening 68 and then lowering the IV bag in the sleeve 62. The sleeve 62 has inwardly inclined inner walls 74 at its lower end 66 which form a reduced neck portion 75 to support the IV bag. The longitudinal opening 68 also allows a visual monitoring of the contents of the IV bag as the entire length of the IV bag is exposed. Since the IV bag is maintained in a cold environment, moisture from the air will not collect on the surface of the IV bag which allows for an unhindered monitoring of the contents of the IV bag.

Figure 4:
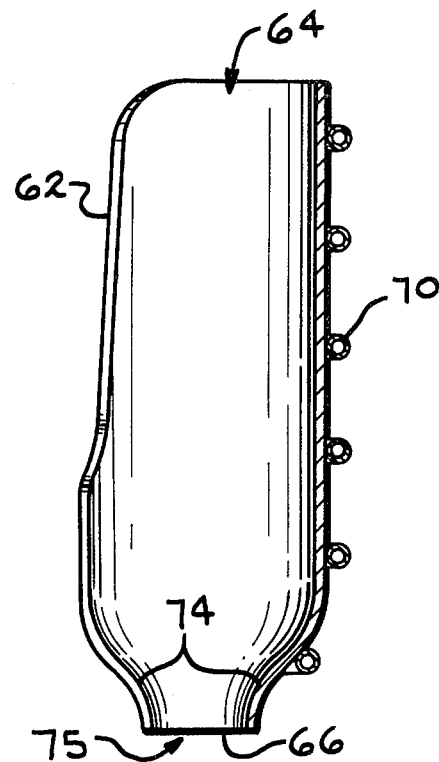
FIG. 4 is a side sectional view of the sleeve evaporator taken substantially from line 4—4 in FIG. 3.
Figure 5:
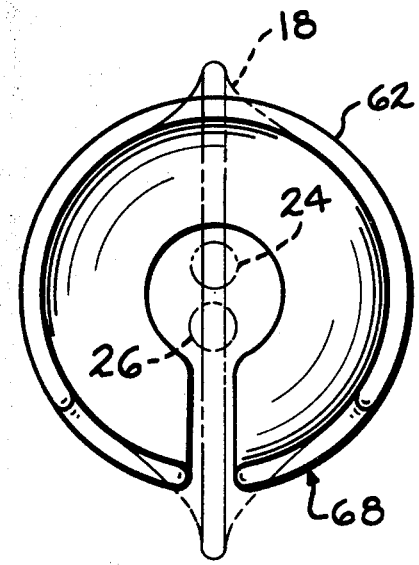
FIG. 5 is a plan view of the sleeve evaporator of the present invention showing an IV bag in broken lines supported in the evaporator.

The tubular sleeve member 62 and the IV bag conform in shape so that a substantial portion of the IV bag is in direct contact with the inner surface of the sleeve member 62 which forms a heat transfer surface. In this manner, efficient conduction of heat from the fluid in the IV bag to the heat transfer surface of the evaporator sleeve member 62 is promoted. A cooling coil or passageway means 70 is connected to refrigeration equipment (not shown) for lowering the temperature of a cooling medium circulating through the coil 70 and is secured to each sleeve 62 so as to substantially surround the sleeve 62 in a serpentine configuration that leaves the opening 68 unobstructed while providing substantial surface to surface engagement between the coil 70 and the sleeve 62 to provide for the efficient conduction of heat from the cardioplegic fluid to the cooling medium in the coil 70. The cooling coil 70 is suitably anchored and also functions to support the sleeve 62 in a generally upright position, as seen in FIG. 4. The IV bag 18 is therefore held in an upright position so that the volume of the fluid of the bag 18 can be monitored as it is withdrawn.

In operation, the IV bags 16 and 18 are placed in their respective sleeve members 62. This can be accomplished by moving the IV bag laterally through the flared portion of the opening 68 and then lowering the IV bag until the reduced neck portion 75 supports the bag. The tubing which forms the passageway loop 28 is connected to the inlet and outlet ports of the IV bag 16 and 18, as seen in FIG. 1, to the pump 32 and to the air trap 36. Prior to administering the cardioplegic fluid, the clamp 48 is clamped to the discharge conduit 46 at the location 80 placing the refrigeration and delivery system 10 in a recirculating mode. The pump 32 is started and circulates and cardioplegic fluid through the tubing 28 from the IV bag 18 back to the IV bag 16 as shown by the arrows in FIG. 1. Consequently, although a substantial portion of the tubing 28 is located outside the chilling zone 14 where the fluid absorbs ambient heat, the recirculation of the fluid back to the IV bags 16 and 18 where the heat is extracted by the evaporator sleeve 62 ensures that chilled cardioplegic fluid is always available in the passageway loop tubing 28. By virtue of the location of the IV bags in the sleeve members 62, there is a substantial surface to surface contact between each IV bag and its respective sleeve member 62 so that the heat absorbed by the cardioplegic fluid in the tubing 28 is quickly transferred to the evaporator sleeve 62.

When the surgeon determines that the cardioplegic fluid is to be administered to the patient, the system 10 is converted to a discharge mode by removing the clamp 48 from the discharge conduit 46 and securing it to the branch 42 at a point downstream of the juncture 40. Chilled cardioplegic fluid is immediately available to be administered to the patient via the discharge conduit 46 and the catheter (not shown). After the predetermined amount of fluid is administered, the clamp 48 is removed from the branch 42 and attached to the discharge tube 46 to return the system to the recirculation mode. A temperature sensing device such as thermister 82 is employed to monitor the temperature of the cardioplegic fluid just prior to its administration to the patient. The thermistor 82 has a sensing probe positioned in the fluid in the air trap 36 to provide accurate temperature readings. The controls on the refrigerator 12 (not shown) can be adjusted to vary the temperature of the fluid as needed. The surface to surface contact between the IV bags and the sleeves 62 facilitates a quick response to an adjustment of the temperature controls.

From the above description, it can be seen that an improved cardioplegic refrigeration and delivery system 10 is provided which enables cardioplegic fluid to be chilled quickly and maintained at a preset temperature and which allows the immediate administration of the chilled cardioplegic fluid without any purging of warm fluid from the tubing. Since the IV bags 16 and 18 are maintained in the refrigerator cabinet, atmospheric moisture does not condense on the bags thereby enabling the unobstructed visual monitoring of the contents in the IV bags 16 and 18. The present invention is effective and frees the operating personnel to concentrate on the surgery.

What is claimed:

1. Apparatus for chilling and dispensing fluid stored in a receptacle unit having an inlet and an outlet and maintaining the fluid at a temperature of a predetermined value, said apparatus comprising a cabinet having an internal chilling compartment, chilling means disposed in said chilling compartment and having a heat transfer surface for absorbing ambient heat, said heat transfer surface and the outer surface of said receptacle unit corresponding at least partially in shape so that said receptacle unit can be disposed in said chilling compartment with said outer surface in direct engagement with said heat transfer surface to enable conduction of heat from said fluid to said chilling means, and dispensing means for discharging chilled fluid from said receptacle unit at a location outside of said chilling compartment, said dispensing means comprising a fluid passageway loop connected to said inlet and said outlet, a portion of said passageway loop being located outside of said chilling compartment, means for circulating said fluid from said outlet through said passageway loop and back to said receptacle unit through said inlet so that said portion of the passageway loop outside of said chilling compartment contains fluid having a temperature value substantially equal to said predetermined valve, and discharge means connected to said portion of said passageway loop selectively operable to discharge chilled fluid from said passageway loop.

2. The refrigeration apparatus according to claim 1, wherein said chilling means comprises a tubular sleeve member formed of material having a high heat conductivity quality.

3. The refrigeration apparatus according to claim 2, wherein said tubular sleeve member includes open ends and a channel extending longitudinally of said sleeve member between said open ends, said sleeve member substantially surrounding said receptacle so that said heat transfer surface engages a substantial portion of the outer surface of said receptacle.

4. The refrigeration apparatus according to claim 3, wherein said fluid receptacle comprises a bag formed of fluid impervious flexible material, said sleeve member having inwardly and downwardly tapered walls adjacent one end thereof forming a reduced neck portion, said sleeve member being located in an upright position in said compartment with said one end forming the lower end of said sleeve member to support said bag upright in said chilling zone.

5. The refrigeration apparatus according to claim 4, wherein said chilling means includes passageway means for conveying a cooling medium in said chilling compartment, said sleeve member being secured to said passageway means to provide for conduction of heat from said bag to said cooling medium.

6. The refrigeration apparatus according to claim 1, wherein said cabinet includes a first access opening, a door formed of transparent material movably mounted on said cabinet between an open position and a closed position overlying said first opening, said transparent door enabling said compartment to be viewed from the outside of said cabinet enabling visual monitoring of the contents of said receptacle.

7. The refrigeration apparatus according to claim 6, wherein said cabinet includes a second access opening, an auxiliary door movably mounted on said cabinet for movement between open and closed positions over said second opening.

8. The refrigeration apparatus according to claim 7, wherein said second opening is disposed below said first opening.

9. Apparatus for delivering chilled intravenous fluid to a patient comprising a refrigerator cabinet having an internal chilling zone, chilling means disposed in said chilling zone and having a heat transfer surface for absorbing ambient heat, receptable means in which said fluid is contained and which has inlet and outlet ports, a fluid passageway loop connected to said inlet and outlet ports, a fluid passageway loop connected to said inlet and outlet ports, a portion of said passageway loop being located outside of said chilling zone, pump means for circulating said fluid from said receptacle means through said passageway loop and back to said receptacle means to insure that the fluid in said outside portion of said loop is chilled, a discharge conduit connected to said outside portion of said loop at a junction between said inlet and outlet ports, flow restrictor means in said passageway loop and on said discharge conduit operable in a discharge mode to close said passageway loop at a location downstream of said junction and to open said discharge conduit to enable delivery of said chilled fluid through said discharge conduit to the patient and operable in a recirculation mode to open said passageway loop and close said discharge conduit to enable recirculation of said fluid through said passageway loop and to said receptacle means.

10. Apparatus according to claim 9, wherein said receptacle conforms in shape to the shape of said heat transfer surface so that said receptacle is disposed in surface to surface contact with said heat transfer surface enabling the conduction of heat from said fluid to said chilling means.

11. Apparatus according to claim 10, wherein said cooling coil means terminates at positions adjacent to said longitudinal opening so that access to said sleeve member can be gained through said opening.

12. Apparatus according to claim 10, wherein said chilling means comprises a tubular sleeve member having open ends, said receptacle being substantially surrounded by said sleeve member so that a substantial portion of the outer surface of said receptacle is in direct contact with said sleeve member.

13. Apparatus according to claim 12, wherein said chilling means includes cooling coil means associated with said sleeve member to form a serpentine configuration in which said coil means substantially surrounds said sleeve member.

14. Apparatus according to claim 12, wherein said sleeve member includes means for supporting said receptacle in an upright position.

15. Apparatus according to claim 14, wherein said support means comprises downwardly and inwardly inclined inner walls on said sleeve member adjacent the lower end thereof, said sleeve member being positioned upright so that said inclined inner walls support said receptacle in said upright position.

16. Apparatus according to claim 15, wherein said sleeve member has a longitudinal opening formed therein extending between the ends thereof enabling the positioning of said receptacle in said sleeve member with said passageway loop connected to said outlet and inlet ports.

17. Heat transfer apparatus for conducting heat to or away from a fluid containing receptacle formed of flexible wall portions, said heat transfer apparatus comprising a tubular sleeve member having open upper and lower ends and being formed of material having a high heat conductivity quality, means forming a reduced neck portion adjacent the lower end of said sleeve member for supporting said receptacle in an upright position, and means forming an opening in said sleeve member intersecting said upper and lower ends thereof, said opening being larger at said upper end of said sleeve than at said lower end to facilitate the insertion of said flexible receptacle into said sleeve member, said sleeve member having a heat transfer surface configured to surround at least partially and to engage directly said fluid containing receptacle thereby to facilitate the transfer of heat to or away from the fluid in the receptacle by conduction.

18. Heat transfer apparatus according to claim 17, wherein said sleeve member includes passageway means through which a heat transfer medium is conveyed to extract heat from or supply heat to said sleeve member.

* * * * *